United States Patent [19]

Heath et al.

[11] Patent Number: 5,977,313
[45] Date of Patent: Nov. 2, 1999

[54] PLATELET SUBSTITUTES AND CONJUGATION METHODS SUITABLE FOR THEIR PREPARATION

[75] Inventors: David Heath; Sarah Margaret Middleton; Roy Harris; Nicola Jane Church, all of Nottingham, United Kingdom

[73] Assignee: Quadrant Healthcare Limited, United Kingdom

[21] Appl. No.: 08/953,514

[22] Filed: Oct. 17, 1997

[30] Foreign Application Priority Data

Oct. 10, 1996 [GB] United Kingdom .................. 9621886
Feb. 10, 1997 [GB] United Kingdom .................. 9702652

[51] Int. Cl.$^6$ ........................ A61K 35/14; A61K 39/385; C07K 17/00
[52] U.S. Cl. ........................ 530/382; 530/331; 530/362; 530/363; 530/380; 530/402; 530/412; 530/427; 424/193.1; 424/194.1; 424/484; 424/499; 514/2; 514/18; 514/773; 514/776; 514/832; 514/965
[58] Field of Search .................................. 530/380, 331, 530/362, 363, 382, 402, 412, 424, 427; 424/193.1, 194.1, 484, 499; 514/2, 18, 773, 776, 832, 965

[56] References Cited

U.S. PATENT DOCUMENTS

| 5,069,936 | 12/1991 | Yen | 427/213.33 |
|---|---|---|---|
| 5,308,620 | 5/1994 | Yen | 424/484 |
| 5,616,311 | 4/1997 | Yen | 424/1.33 |
| 5,725,804 | 3/1998 | Yen | 252/314 |

FOREIGN PATENT DOCUMENTS

| 0 494 417 | 7/1992 | European Pat. Off. . |
|---|---|---|
| WO 92/13495 | 8/1992 | WIPO . |
| WO 92/18164 | 10/1992 | WIPO . |
| WO 96/15814 | 5/1996 | WIPO . |
| WO 96/18388 | 6/1996 | WIPO . |
| WO 96/39128 | 12/1996 | WIPO . |

OTHER PUBLICATIONS

Agam, G. and Livne, A., "Passive Participation of Fixed Platelets in Aggregation Facilitated by Covalently Bound Fibrinogen," *Blood 61(1)*: 186–191 (1983).

Agam, G. and Livne, A., "Platelet–Platelet Recognition During Aggregation: Distinct Mechanisms Determined by the Release Reaction," *Thrombosis and Haemostasis 51(2)*: 145–149 (1984).

Agam, G. and Livne, A., "Resolution and Reconstitution of Interplatelet Recognition During Aggregation," *Thrombosis and Haemostasis 59(3)*: 504–506 (1988).

Agam, G. and Livne, A., "Erythrocytes with covalently bound fibrinogen as a cellular replacement for the treatment of thrombocytopenia," *Euro. J. Clin. Invest.* 22:105–112 (1992).

Coller, B. S., "Interaction of Normal, Thrombasthenic, and Bernard–Soulier Platelets With Immobilized Fibrinogen: Defective Platelet–Fibrinogen Interaction in Thrombasthenia," *Blood 52(2)*: 169–178 (1980).

Coller, B. S. et al., "Thromboerythrocytes," *J. Clin. Invest.* 89:546–555 (1992).

Dardik, R. et al., "Platelets Mediate Tumor Cell Adhesion to the Subendothelium Under Flow Conditions: Involvement of Platelet GPIIb–IIIa and Tumor Cell $\alpha_v$ Integrins," *Int. J. Cancer* 70:201–207 (1997).

Yen, R. C. K. et al., "A New Hemostatic Agent: Thrombospheres Shorten the Bleeding Time (BT) in Thrombocytopenic Rabbits," XVth Congress of the International Society on Thrombosis and Haemostasis, Jerusalem, Israel, Jun. 11–16, 1995 (Abstract).

D'Souza et al, *The Journal of Biological Chemistry*, vol. 263, No. 8 pp. 3943–3951, Mar. 15, 1988.

*Primary Examiner*—Cecilia J. Tsang
*Assistant Examiner*—Abdel A. Mohamed
*Attorney, Agent, or Firm*—Sterne, Kessler, Goldstein & Fox P.L.L.C.

[57] ABSTRACT

Platelet substitutes, comprising fibrinogen, or analogous products useful in therapy, which further comprise an insoluble carrier to which is bound an essentially non-degraded active protein including the sequence Arg-Gly-Asp. Such conjugates can be made by a conjugation process comprising 0.01 to 2.5% by weight active fibrinogen, and no more that 50% inactive fibrinogen.

28 Claims, No Drawings

PLATELET SUBSTITUTES AND CONJUGATION METHODS SUITABLE FOR THEIR PREPARATION

FIELD OF THE INVENTION

This invention relates to platelet substitutes, i.e. compositions comprising fibrinogen, and also to conjugation methods that can be used, inter alia, to bind fibrinogen to a particulate carrier.

BACKGROUND OF THE INVENTION

Covalently-bound conjugates, comprising an active drug and a carrier, are useful as a means of delivering the drug, e.g. to a specific site of action. Albumin has been proposed as a carrier for this purpose. Microparticles of albumin, their production and use as a carrier, are described in WO-A-9618388.

The covalent attachment of large peptides and proteins to human serum albumin (HSA) microcapsules can generate a number of problems. Sufficient binding sites may not be available for cross-linking due to poor contact between the protein and the microcapsule surface. Also, intra-rather than intermolecular cross-linking is difficult to control when using short or zero length cross-linkers such as glycolaldehyde or EDC, respectively. This can lead to low loading of microcapsules and inactivation of the protein.

Agam and Livne, in a series of papers, Blood 55:186–191 (1983), Thromb. Haemostasis 51:145–9 (1984) and 59:504–6 (1988), and Eur. J. Clin. Invest. (1991), showed that fibrinogen coated on fixed platelets augmented platelet aggregation, and that fibrinogen-coated erythrocytes reduced bleeding times in thrombocytopenic rats. Fixation involved the use of formaldehyde.

Coller et al, J. Clin. Invest. 89:546–555 (1992), describe "Thromboerythrocytes", an autologous, semi-artificial alternative to platelet transfusions. In order to avoid the limitations and drawbacks of using fresh platelets, erythrocytes were coupled to peptides containing the RGD cell recognition sequence, using a bifunctional cross-linker.

In an abstract presented to the XVth Congress of the International Society on Thrombosis and Haemostasis, Jerusalem, Israel, on Jun. 11–16, 1995, Yen et al reported the haemostatic potential of "Thrombospheres", i.e. cross-linked HSA microspheres, mean diam. 1.1–1.3 $\mu$m, with human fibrinogen covalently bound to their surfaces. In a thrombocytopenic rabbit model, ear bleeding times were reduced. The HSA microspheres were reportedly prepared by the procedure described in U.S. Pat. No. 5,069,936, i.e. a solution/desolvation process using glutaraldehyde as a cross-linking agent, ethanol to cause precipitation, and a surfactant to modify the surface of the cross-linked protein molecules. These steps do not provide size control of the microspheres, may cause bound protein to be degraded, and are unsuitable for large-scale manufacture of platelet substitutes.

U.S. Pat. No. 5,069,936 describes the covalent bonding of various biological molecules, but not fibrinogen. A polyaldehyde is proposed as a covalent linking agent. Examples 12 and 14 use glutaraldehyde to bind antibody and enzyme (alkaline phosphatase), respectively.

WO-A-9639128 (published Dec. 12, 1996) also describes "Thrombospheres". Again, no specific preparation is given.

Fibrinogen is an adhesive glycoprotein containing the sequence RGD(S). It and other such glycoproteins (including fibronectin and collagen, among others) may mediate the adhesion of tumour cells to sub-endothelial layers. These glycoproteins interact with integrins found in tumour cells, e.g. the fibronectin receptor, and the GPIIb/IIIa receptor on platelets; see Dardik et al, Int. J. Cancer 70:201–7 (1997).

One of the major problems in the surgical treatment of cancers is the increased risk of tumour cells being released into the circulatory system. This is one reason for increased morbidity in patients with prostate cancer, after surgery. It would be desirable to remove circulating metastatic tumour cells, or inhibit their deposition on vascular surfaces.

SUMMARY OF THE INVENTION

According to one aspect of the present invention, a new method for attaching peptides (by which is meant any peptide, polypeptide, protein or conjugate thereof) such as fibrinogen to microcapsules allows a spacer (e.g. small peptide or fatty acid) to be inserted between the protein and microcapsule. More specifically, the invention utilises the fact that a carrier such as HSA has free thiol groups, with which a bifunctional compound can react, the bifunctional compound having one group selectively reactive with the active component (drug) to be conjugated.

By virtue of the invention, controllable cross-linking can be achieved due to the specificity of one of the linking groups for the free thiol group available on carriers such as HSA. Controllable cross-linking is one important aspect of the present invention, since it may have a direct bearing on the activity of the attached molecule.

The spacer can include enzyme-cleavable peptides, acid or alkali-labile bonds and be of variable length, depending on the requirements of the application. The length of the spacer may be another important aspect of this invention, as it may determine the conjugate's ability to target receptors, such as fibrinogen to GPIIb/IIIa.

According to a second aspect of the invention, e.g. by using the novel method, a novel pharmaceutically-acceptable product has utility as platelet substitutes. Such a product comprises an insoluble carrier, e.g. stabilised albumin, to which fibrinogen is bound, essentially without loss of the fibrinogen's activity. Binding may be non-chemical, e.g. by adsorption or chemical, e.g. using a linker at least 10 nm long.

This invention provides, for the first time, pure, robust, therapeutically-acceptable, platelet substitutes. Purity may be embodied in the absence of chemical cross-linker and/or surfactant. They are suitable for use in the treatment of thrombocytopenia.

It is an additional feature of the invention that, because fibrinogen acts as a targeting agent, products of the invention may usefully have other bound active agents. Such agents will be chosen with regard to the site of action, usually a wound or other bleeding locus, and to the nature of the problem that is addressed.

DESCRIPTION OF THE INVENTION

The carrier that is used in the invention is preferably produced by spray-drying, under conditions that allow good control of particle size and size distribution. For example, the preferred size is up to 6 $\mu$m, e.g. 1 to 4 $\mu$m, in order that the particles can pass through capillaries.

Suitable materials and procedures, and also methods for stabilising the microparticles, by heat or by chemical cross-linking, are fully described in WO-A-9218164, WO-A-9615814 and WO-A-9618388, the contents of which are incorporated herein by reference. As explained in the latter publication, the conditions that are described do not affect functional groups, such as the thiol groups in albumin, which therefore remain available for reaction with biological molecules.

The microparticles used in this invention may have the physical characteristics described in the two publications identified above, e.g. being smooth and spherical, and containing air. In order to obtain insoluble, cross-linked microcapsules, the spray-dried product may be reacted with a chemical cross-linking agent. However, heat and γ-irradiation are preferred, and may also sterilise the dry powder products.

In one embodiment of the invention, fibrinogen (or another RGD peptide) may be bound to such a carrier without a linker, e.g. by adsorption. This may be achieved by precipitation of the peptide on to the surface of the microspheres, e.g. by control of pH and other conditions, as will be evident to one of ordinary skill in the art. Excess/unbound fibrinogen is then washed away.

In another embodiment, fibrinogen is bound using a conventional bifunctional reagent such as a polyaldehyde. Glycolaldehyde is preferred. Another example of a spacer is sulfosuccinimidyl 4-(iodoacetyl)aminobenzoate (which is water-soluble). Its length is approx. 1 nm.

In the conjugation process that is defined above as the first aspect of the invention, the bound peptide comprises preferably at least fibrinogen. Other examples are Factor VIII, Factor IX, other blood factors, proteins of the coagulation cascade, thrombolytic agents, antibodies, α-1-antitrypsin. By providing a combination of, say, fibrinogen and Factor VIII, the products of the invention may be useful in the treatment of haemophilia. In addition, or as an alternative, to the use of a thrombolytic drug such as urokinase; blood clots may be treated by the use of ultrasound. For this purpose, the air-containing microcapsules of this invention are especially suitable.

The bifunctional compound (say, $Y^1$—Y—$Y^2$) that is used in the invention may itself be generated by reaction of simpler compounds $Y^1$—$Y^3$—$Y^4$ and $Y^5$—$Y^6$—$Y^2$, wherein $Y^1$ is the thiol-specific reactive group, $Y^4$ and $Y^5$ react together so that $Y^3$ and $Y^6$ together are the spacer Y, and $Y^2$ is the drug-reactive group. Thus, for example $Y^1$ is thiol-reactive I and/or $Y^4$ is COOH, as in $ICH_2COOH$. More specifically, iodoacetic acid is activated by the addition of EDC (N-hydroxysuccinimide can be included to assist in the EDC-catalysed amidation reaction, resulting in the formation of an active succinimidyl ester). The activated species is then incubated with a peptide or molecule having free amino ($Y^5$) and carboxyl ($Y^2$) terminal groups. A suitable peptide comprises, say, 3 to 6 amino-acids such as Gly or Ala.

The carboxyl group of this intermediate conjugate is then activated with EDC. The activated spacer is incubated with the protein and a peptide bond is formed with the lysine amino side-chains of the protein. Only one end of the spacer can be attached to the protein and, therefore, no cross-linking can occur at this time. Most plasma proteins do not contain free thiol groups, HSA being an exception, and, therefore, intramolecular cross-linking of the protein is avoided.

By way of example, the spacer has an N-terminal iodoacetyl functionality which will react selectively with the free thiol located at the Cys-34 residue of HSA microcapsules. The spacer may also have a free carboxylic acid which can be activated, e.g. using 1-ethyl-3,3-dimethylamino propylcarbodiimide (EDC), and linked to the amine groups on a peptide.

The activation of the spacer with EDC may be performed at pH 6 in 0.05M 4-morpholinoethanesulfonic acid buffer (MES buffer). In order to prevent any adsorption of fibrinogen occurring, once fibrinogen has been reacted with the activated N-iodoacetyl peptide, e.g. Gly-Leu-Phe, the buffer is changed to 0.1M sodium borate buffer at pH 8. The adsorption of fibrinogen does not occur at this higher pH. Any binding of fibrinogen to HSA microcapsules will occur only as a result of the free thiol from HSA microcapsules reacting with the carbon atom adjacent to the iodine molecule on the N-terminal end of the spacer. The optimum pH for the thiol-iodine interaction is pH 8.

In order to enhance the binding of fibrinogen (by way of example) via the spacer onto the microcapsules, the free thiol content of the microcapsules may be increased using Traut's reagent (2-iminothiolane). This reagent modifies the ε-amino groups of lysine into thiol groups, resulting in an increase in the number of free thiols available to bind with the spacer and thus fibrinogen.

Increased loading may also be achieved by cross-linking thiol-containing amino-acids or peptides to the microcapsules prior to attaching the protein of interest (e.g. cysteine, reduced glutathione). Chemical linkers such as iminothiolane can be used to introduce (as well as increase the number of) thiol groups. Other proteins could be used to produce microcapsules if thiol groups were added to their surface, as an alternative to using the inherent properties of HSA (i.e. free thiol groups).

The protein plus spacer is then incubated with HSA microcapsules containing free thiol groups. The preparation of such microcapsules by spray-drying, without loss of functional groups, is described in WO-A-9615184 and WO-A-9618388.

The molar ratio of spacer to protein should be high enough to allow sufficient groups to be attached to the protein for cross-linking to microcapsules, but low enough not to deactivate the protein. This specific procedure generates the intermediate conjugate $ICH_2CO(A)_nCOOH$ wherein $(A)_n$ represents n residues of the same or different amino-acids. Choice of n controls of the length of the spacer, e.g. 10 to 600 nm (1 to 60 Angstrom), depending on the intended application, often at least 50 nm.

The process steps described above can be conducted in mainly aqueous-based solvent systems. Reaction by-products can be easily removed.

The cross-linking technology should allow controllable linking of peptides and proteins to microcapsules, better retention of protein activity and the ability to modify the spacer in terms of length and cleavability.

As indicated above, products of the invention containing fibrinogen may act at the side of tumours. Therefore, they may be used in tumour therapy, e.g. by linking a cytotoxic agent by the particular method of this invention or by the methods described in WO-A-9618388. Suitable cytotoxic agents include methotrexate, doxorubicin, cisplatin or 5-fluoro-2-deoxyuridine.

The targeting of drugs to tumour cells may be achieved using products of the invention as vehicles reacting directly with the cells or by participating in the aggregation and deposition of fibrin at the site of cell adhesion.

Products of this invention may be loaded with cytotoxic agents or a combination of cytotoxic and targeting agents. They may then be used to target the disseminated tumour cells in the circulation, by specific interactions with the cell glycoprotein receptors (seek and destroy) or by participation in the platelet aggregation process at the site of adhesion. In both cases, the cytotoxic drug is concentrated at the site of the invading tumour cells.

Alternatively, tumour aggregation may be inhibited in the circulatory system or even at the site of adhesion, by coating the tumour cell surface with products of the invention, and blocking the sites/mechanisms that activate platelets. This would then allow the body's natural defence mechanisms to facilitate the removal of the tumour cells.

Products containing, for example, the GPIb receptor (interacts with von Willebrands factor) or receptors for collagen or other sub-endothelial matrix components may also be delivered, to potentially block the binding sites for tumour cells by coating the sub-endothelial matrices. The product should still allow an interaction with platelets at the site of a wound, but should also restrict the invasion of vascular wall by any immobilised tumour cell.

An important advantage of the present invention is that the activity of fibrinogen (or other RGD peptide) can be substantially retained. The content of active fibrinogen can be determined by ELISA for fibrinopeptide A (FPA).

In an assay for FPA, incubation of a constant amount of excess fibrinopeptide A antibody with the sample (or standard) leads to formation of an antigen-antibody complex. The concentration of the residual excess antibody is inversely proportional to the amount of FPA in the sample (or standard).

To determine the concentration of antibody, aliquots of the incubation mixture are transferred, for subsequent incubation, into reaction vessels coated with excess FPA. The wall-bound antigen-antibody complexes obtained form sandwich complexes with peroxidase-labelled anti-IgG antibodies. The amount of these complexes provides a direct measure of the FPA concentration in the sample.

The sandwich complexes obtained are determined by enzymatic reaction of peroxidase with $H_2O_2$/ortho-phenylenediamine (chromogen) and subsequent spectrophotometric measurement at 492 nm. Owing to the inverse relationship of bound enzyme activity and antigen concentration, the absorbances measured decrease as the FPA concentration in the sample increases. The results are evaluated by constructing a reference curve with standards of known concentrations.

A platelet substitute of the invention usually comprises at least 0.01%, preferably at least 0.015%, more preferably at least 0.02%, and most preferably at least 0.025%, active fibrinogen. The amount of fibrinogen should not be too great, in order to avoid aggregation, e.g. up to 1, 1.5, 2 or 2.5%. Of the fibrinogen content, it is desirable that at least 50%, preferably at least 70%, more preferably at least 90%, should be active. This can be determined with respect to the total content of fibrinogen, which again can be measured by method such as ELISA. Total fibrinogen may also be determined by radio-labelling, e.g. with $^{125}I$, and counting, by conventional procedures.

The fibrinogen may be blood-derived, transgenic or recombinant, full-length or any active fragment thereof. Fragments are disclosed, inter alia, by Coller et al, supra.

For use as a therapeutic agent, a product of the invention may be administered as is, or mixed with any suitable carrier known to those of ordinary skill in the art. The amount of the product administered will be determined largely to the severity of the wound or other condition to be treated. A typical dosage may be $1.5 \times 10^9$ microcapsules per kg body weight.

The following Examples illustrate the invention.

The fibrinogen used in the Examples was a full-length, blood-derived, commercially available product that had been doubly virally-inactived.

HSA microcapsules used in the Examples were prepared by spray-drying and were then stabilised by heating, as described in WO-A-9615814. The microcapsules were sunk with 1% Tween 80 and washed extensively with PFPW to remove Tween 80 and excipient prior to use.

PFPW=pyrogen-free purified water.

DTNB=5,5-dithiobis(2-nitrobenzoic acid).

Free thiol content was measured using the Ellman assay with DTNB. This reagent participates in a thiol exchange mechanism with any free thiols present on the protein under examination, and releases (TNB) which can be measured at 412 nm using UV/VIS spectrophotometry.

EXAMPLE 1

Iodoacetic acid N-hydroxysuccinimide ester (IAAE) was reacted with tetra-alanine (AAAA) in a mixture of methanol and distilled water for 1 hour at room temperature. EDC was added in a 1.2 molar ratio when compared with AAAA in distilled water for 5 minutes after which fibrinogen, which had been resuspended in distilled water, was added. After stirring for 1 hour at room temperature, microcapsules were added, and the mixture was stirred at room temperature for a further 16 hours.

The microcapsules were washed 6 times with distilled water post-reaction to remove any unreacted fibrinogen and spacer, and were then resuspended in distilled water to give a final microcapsule concentration of 100 mg/ml.

The amount of fibrinogen used (54 mg) was calculated to be 0.5 molar equivalents when compared with microcapsules (20 mg). This was deemed the maximum loading possible given the free thiol content of the microcapsules.

ELISA results revealed that a fibrinogen loading of 0.5 mg per 100 mg HSA had been achieved. A slide test performed using 5 mg labelled microcapsules and 0.15 units of thrombin gave a positive result. Aggregation occurred immediately on addition of thrombin.

A control experiment was also performed using the same quantities of microcapsules and fibrinogen without IAAE, AAAA or EDC. ELISA results from this sample showed that a fibrinogen loading of 0.06 mg per 100 mg HSA had been achieved. This had arisen without the use of a cross linker. The sample also gave a positive slide test result, but aggregation did not occur until approximately 12 seconds after the addition of thrombin.

EXAMPLE 2

The procedure of Example 1 was repeated, but in order to optimise the reaction between IAAE and AAAA, it was followed using reverse-phase HPLC. For this purpose, it was necessary to investigate the amount of AAAA required to convert all IAAE into product. Any unreacted IAAE could possibly participate in unwanted side reactions further on into synthesis. Consequently, the amount of AAAA reacted was increased from 1 molar equivalent to 4, whilst the amount of IAAE used was kept constant.

EXAMPLE 3

The procedure of Example 1 was repeated, but the amount of spacer required for a given quantity of fibrinogen was investigated using a ratio of IAAE to AAAA of 1:4 and an EDC excess of 1.2 molar equivalents with respect to AAAA. The amount of spacer used was calculated using the number of moles of IAAE present, since this is the active constituent and limiting factor of the spacer preparation. The ratio of IAAE-AAAA-EDC to fibrinogen was thus increased from 1:1 to 1:5.

ELISA results revealed that a ratio of fibrinogen to IAAE-AAAA-EDC of 1:2 reproducibly yielded the highest loading of fibrinogen. The loading was calculated to be 0.06 mg per 100 mg HSA and the sample aggregated within 5 seconds using the slide test assay.

EXAMPLE 4

In a further optimisation experiment, Example 1 was repeated but with a reduced amount of fibrinogen. The ratio of IAAE-AAAA-(EDC)-Fibrinogen to microcapsules was varied, using 0.5, 0.3, 0.1, 0.05 and equivalents.

ELISA results revealed all samples except the 1:0.01 ratio had an acceptable loading of fibrinogen. The samples varied between 0.1 and 0.2 mg fibrinogen per 100 mg HSA, and the experiment showed that reducing the amount of fibrinogen to only 0.05 molar equivalents yielded as high loading as using 0.5 molar equivalents.

EXAMPLE 5

As the results achieved in Example 4 were fairly uniform, two experiments were conducted. Table 1 shows the quantities used to investigate the fibrinogen loadings for the first experiment using the following ratios:

IAAE:AAAA (1:4)
IAAE-AAAA-EDC:Fibrinogen (2:1)
IAAE-AAAA-(EDC)-Fibrinogen: Microcapsules (0.3:1)

Table 2 summarises the quantities required for the second experiment which used the same quantities as the first experiment except:

IAAE-AAAA-(EDC)-Fibrinogen:Microcapsules (0.05:1)

TABLE 1

| Reagent | Quantity | Number nmoles |
| --- | --- | --- |
| IAAE | 52 µg | 182 |
| AAAA | 210 µg | 695 |
| EDC | 160 µg | 834 |
| Fibrinogen | 31 mg | 91 |
| Microcapsules | 20 mg | 303 |

TABLE 2

| Reagent | Quantity | Number nmoles |
| --- | --- | --- |
| IAAE | 8.6 µg | 30.4 |
| AAAA | 35 µg | 115.8 |
| EDC | 26.6 µg | 139 |
| Fibrinogen | 5.2 mg | 15.2 |
| Microcapsules | 20 mg | 303 |

In both experiments the microcapsules were reacted with the spacer in 0.1 M sodium phosphate, 0.15 M sodium chloride buffer at pH 8 at room temperature for 16 hours. The microcapsules were then washed extensively with PFPW and resuspended to give a final microcapsule concentration of 100 mg/ml.

The ELISA results obtained for the 0.3 and 0.05 ratio samples revealed 0.38 and 0.42 mg fibrinogen was bound per 100 mg HSA respectively. The slide test results for both samples gave positive results with aggregation occurring approximately 2 seconds after the addition of thrombin.

EXAMPLE 6

1 mg/ml tetra-alanine (AAAA) is prepared. 3 mg tetra-alanine (Sigma) is weighed into a 7 ml bijou, dissolved in 3 ml PFPW, and vortexed.

3 mg/ml Iodoacetic Acid N-hydroxy Succinimide Ester (IAAE) is prepared. 3 mg (Sigma) is weighed out into a 7 ml bijou and dissolved in 1 ml of methanol. This is vortexed.

70 µl of the tetra-alanine is pipetted into a 7 ml bijoux followed by 5.7 µl of IAAE. This is vortexed. The molar ratio of the IAAE to the tetra-alanine is 1:4.

2.3 g microcapsules is formulated with glucose. The mixture consists of approximately 800 mg protein and 1600 mg glucose. A 50 mg/ml protein concentration is prepared in 1% (v/v) Tween 80 (Sigma).

The contents are vortexed and allowed to stand for approx. 30 minutes at room temperature, to sink the hollow microcapsules. A 400 µl aliquot is added into an Eppendorf after vortexing. The sample is centrifuged at 3000 rpm for 2 minutes in a Beckmann GS-15 at room temperature (Relative Centrifugal Force RCF=1502 radians/sec). This is then washed with 1 ml of PFPW 3 times. The pellet is stored at room temperature until required.

A vial of human fibrinogen is reconstituted in 20 ml 0.1M saline/0.025M sodium phosphate buffer (pH 7.2) which produces a theoretical fibrinogen concentration of 60 mg/ml. Fibrinogen solution is made 5.8% (w/v) w.r.t PEG 1000 by addition of 4 ml of buffered 35% (w/v) PEG solution. The resulting solution is mixed by inversion only and then chilled on ice for 15–20 minutes. The resulting precipitate is centrifuged (4000 rpm/4 minutes/Beckman GS15). The supernatant is removed and the volume is measured.

The pellet is then washed by addition of 7% (w/v) PEG/0.1M saline/0.025M sodium phosphate buffer pH 7.2). Half the volume of the original stock fibrinogen is used to wash the pellet. The pellet is resuspended in the buffer and mixed with a cuvette stirrer. The solution is centrifuged at 4000 rpm for 4 minutes. The supernatant is removed from the washed pellet and the volume is measured. The pellet is reconstituted in 20 ml 0.025M sodium phosphate/0.1M saline buffered at pH 7.2. The volume of the purified fibrinogen solution is measured. The total protein concentration is determined by the BCA assay. The fibrinogen concentration is calculated by reading the UV absorbance at 280 nm. Since a 1% (w/v) fibrinogen solution is known to have an extinction coefficient of 15.5 at 280 nm, the concentration of fibrinogen can be calculated. (Ref Haemostasis and Thrombosis, Volume 1, 3rd Edition, Page 492, R. F. Doolittle).

1 mg/ml EDC is prepared fresh in PFPW. 3 mg EDC (Sigma) is weighed into a 7 ml bijou and dissolved in 3 ml PFPW. This is vortexed. The bijou containing the reacted spacer is removed from the stirrer. 53 µl of the EDC is added into the reaction mixture. The molar ratio of EDC to tetra-alanine is 1:1.2. This is vortexed and stirred for c. 5 minutes.

10.3 mg fibrinogen is added in 258 µl at 40 mg/ml. The molar ratio of fibrinogen to HSA microcapsules is 0.1:1. The molar ratio of IAAE to fibrinogen is 2:1. The bijou is inverted and stirred for c. 60 minutes.

20 mg washed microcapsules are resuspended in buffer, i.e. 0.1M disodium hydrogen phosphate/0.15M NaCl at pH 8.0. The pH is adjusted with 12N HCl. 613 µl of buffer is added into the microcapsules. This is added into the reaction mixture of 387 µl. This makes a final volume of 1 ml. This is stirred overnight at room temperature. This reaction is approximately 16 hours.

The bijou is removed from the stirring plate. It is centrifuged at 4500 rpm for 1 minute (RCF=3379 radians per sec). The supernatant is removed to be analysed by ELISA.

The pellet is washed 6 times in 1 ml of PFPW. The washings are also kept for ELISA to determine a mass balance. The pellet is then resuspended in 200 $\mu$l of PFPW. A sample is provided for ELISA (100 $\mu$l) and slide test determination (100 $\mu$l).

Samples of product are stored at 4° C.

EXAMPLE 7

One vial of formulated microcapsules is prepared, containing approximately 1 g of protein and 2 g of mannitol. Irradiated vials are stored at 4° C. A 50 mg/ml protein concentration is prepared in 1% (v/v) Tween 80. The contents are vortexed and allowed to stand for c.30 minutes at room temperature to sink the hollow microcapsules.

For a 1 g preparation a 20 ml aliquot is added into a 50 ml Beckman centrifuge tube after vortexing. This is centrifuged in the Beckman Avanti J-25 at 5000 rpm for 3 minutes at room temperature (Relative Centrifugal Force RCF=4648 radians/second). This is then washed with 20 ml of PFPW 2 times with centrifugation at 3300 rpm for 2 minutes at room temperature (RCF=2025 radians/second).

The microcapsules are washed finally with 20 ml of 10 mM phosphate buffer (pH 6.0) with centrifugation at 3300 rpm for 2 minutes at room temperature (RCF=2025 radians/second). The pellet is resuspended in 20 ml of 10 mM phosphate buffer (pH 6.0) and transferred to a 70 ml Sterilin container with a magnetic stirrer.

Fibrinogen is reconstituted in WFI to produce a theoretical fibrinogen concentration of approximately 40 mg/ml. The suspension is mixed gently on a roller mixer for 20 minutes. Fibrinogen that is excess is flash frozen in liquid nitrogen in cryogenic nalgene vials and stored (−20° C.).

For a 1 g preparation, fibrinogen is added (0.25 ml at 40 mg/ml) to the microcapsules, with stirring. The molar ratio of fibrinogen to HSA microcapsules is 0.002:1. The mixture is stirred for c. 4 hours.

The container is removed from the stirring plate and the contents transferred into a Beckman 50 ml tube. It is centrifuged at 3300 rpm for 2 minutes at room temperature (RCF=2025 radians/second). The supernatant is discarded. The pellet is washed 3 times in 20 ml of WFI. The washings are discarded. The pellet is then resuspended to 10 ml using WFI. A 500 $\mu$l sample is provided for ELISA, slide test determination and Coulter Counting.

On completion of the Coulter Count, the sample is formulated by the addition of stock mannitol (153 mg/ml) and stock phosphate buffer (250 mM) to achieve isotonic mannitol (51 mg/ml), 25 mM phosphate buffer (pH 7.0±0.2) and a count of 1500 million microcapsules/ml.

EXAMPLE 8

HSA microcapsules (50 mg, 0.757 $\mu$mol) were resuspended in 0.1M sodium borate buffer, pH 8.05 (832 $\mu$l), and 2-iminothiolane (520 $\mu$g, 3.78 $\mu$mol) in 0.1M sodium borate buffer, pH 8.05 (168 $\mu$l), was added. The reaction was stirred for one hour at room temperature after which the microcapsules were washed in distilled water (5×5 ml). The microcapsules were given a final wash in 0.1M sodium borate buffer, pH 8.05 and resuspended in the same buffer (2 ml).

Control

Fibrinogen (20 mg, 0.058 $\mu$mol) was resuspended in 0.05M MES buffer, pH 6.03 (1.2 ml) and was stirred at room temperature for 2 hours. HSA microcapsules (50 mg, 0.757 $\mu$mol), were added in 0.1M sodium borate buffer, pH 8.05 (2 ml), and the reaction stirred for a further 2 hours at room temperature.

EXAMPLE

N-Iodoacetyl Gly-Leu-Phe (3 mg, 5.95 $\mu$mol) was resuspended in 0.05M MES, pH 6.03 (1.2 ml) and EDC (2 mg, 10.4 $\mu$mol) was added and the reaction was stirred for 5–7 minutes at room temperature. Fibrinogen (20 mg, 0.058 $\mu$mol) was added and the mixture was stirred for 2 hours at room temperature. HSA microcapsules (50 mg, 0.757 $\mu$mol) in 0.1M sodium borate buffer, pH 8.05 (2 ml) were added, and the reaction was stirred for a further 2 hours at room temperature.

A sample was removed from each of the control and experimental reactions for free thiol determination. The remaining sample of control and experimental material was washed with distilled water (2×5 ml) and resuspended to give a HSA microcapsule concentration of 100 mg/ml.

In this Example, the free thiol content of HSA microcapsules was increased from 0.211 to 1.73 nmole SH per nmole HSA. No effect on the activity of the control sample (no spacer) was seen. However when the modified microcapsules were reacted with fibrinogen which had been incubated with the spacer, an active sample was obtained by slide test. The slide test activity increased to 5–15 secs with HSA microcapsules with a higher free thiol content. This suggests that increasing the free thiol content of HSA microcapsules leads to an increased activity of the final product, due to the fact that an increased binding of spacer and thus fibrinogen can be achieved.

EXAMPLE 9

EDC (69.8:1 of a 0.5 mg/ml solution in water) was added to N-iodoacetyl tetraglycine (125.5:1 of a 0.5 mg/ml solution in water) and the mixture stirred for 5 minutes at room temperature. Fibrinogen (186:1 of a 55.5 mg/ml solution) was added and the reaction stirred for 1 hour at room temperature.

Doxorubicin-loaded microcapsules, containing 0.56 moles drug per mole HSA (100 mg), resuspended in 1.619 ml water, were added to the activated fibrinogen solution. The mixture was stirred at room temperature for 16 hours.

The microcapsules were collected by centrifugation at 3500 rpm for 2 minutes and the supernatant removed and discarded. The microcapsules were washed in water (4×5 ml) and resuspended in 1 ml water to give a final HSA concentration of approximately 100 mg/ml.

The sample was tested for activity, and it was found that the addition of fibrinogen did not result in the loss of any doxorubicin from the microcapsules. Further, the double-loaded microcapsules displayed activity with thrombin, indicating that the bound fibrinogen has remained active despite the presence of doxorubicin. The levels of fibrinogen present were determined using ELISA. These results have shown a reasonable loading of fibrinogen.

We claim:

1. A pharmaceutically-acceptable product comprising an insoluble carrier to which is bound an essentially non-degraded active protein selected from fibrinogen and fragments thereof having platelet aggegation activity.

2. A product according to claim 1, wherein the binding is by adsorption.

3. A product according to claim 1, wherein the binding is covalent, via a chemical linker, in the absence of surfactant.

4. A product according to claim 1, wherein the binding is covalent, via a chemical linker at least 10 nm long.

5. A product according to claim 1, further comprising a bound cytotoxic agent.

6. A product according to claim 1, wherein the carrier comprises cross-linked protein microparticles.

7. A product according to claim 6, wherein the protein of the microparticles is albumin.

8. A product according to claim 1, wherein the fibrinogen is full-length.

9. A product according to claim 8, which comprises 0.01 to 2.5% by weight active fibrinogen, and no more than 50% inactive fibrinogen.

10. A method for preparing a covalently-bound conjugate of the formula X—S—Y—Z, wherein X is a carrier component, S is a sulfur atom, Y is a spacer and Z is an active component, which comprises the steps;

(i) reacting the active component with a bifunctional reagent of the formula $Y^1$—Y—$Y^2$, wherein $Y^1$ is a group selectively reactive with free thiol groups and $Y^2$ is a group reactive with the active component but not with the thiol groups; and (ii) reacting the resultant $Y^1$—Y—Z with the carrier component having free thiol groups.

11. A method according to claim 10, wherein $Y^2$ is COOH.

12. A method according to claim 10, wherein the spacer comprises a fatty acid or peptide chain.

13. A method according to claim 10, wherein the active component has $NH_2$ groups.

14. A method according to claim 10, wherein the spacer is 10 to 600 nm long.

15. A method according to claim 10, wherein the carrier component is in the form of microparticles.

16. A method according to claim 10, wherein $Y^1$ is I.

17. A method according to claim 16, wherein the bifunctional reagent is obtained by reaction of a spacer component with activated iodoacetic acid.

18. A method according to claim 10, wherein the active component is a protein including the sequence Arg-Gly-Asp.

19. A method according to claim 18, wherein the protein is fibrinogen.

20. A method according to claim 10, wherein the carrier is albumin.

21. Albumin conjugated via its thiol groups to an active component by means of a spacer at least 50 nm long produced by the method according to claim 20.

22. A method according to claim 20, wherein the carrier is human serum albumin.

23. Albumin conjugated via its thiol groups to an active component by means of a spacer at least 50 nm long produced by the method of claim 22.

24. Albumin conjugated via its thiol groups to an active component selected from fibrinogen and fragments thereof having platelet aggregation activity, by means of a spacer at least 50 nm long.

25. Albumin according to claim 24 wherein the albumin is in the form of microparticles.

26. Albumin conjugated according to claim 21, further comprising a bound cytotoxic agent.

27. Albumin according to claim 24, wherein the fibrinogen is full-length, for use as a platelet substitute.

28. Albumin according to claim 27, wherein the fibrinogen comprises 0.01 to 2.5% by weight active fibrinogen, and no more than 50% inactive fibrinogen.

* * * * *